United States Patent
Brown et al.

(10) Patent No.: US 11,357,591 B2
(45) Date of Patent: Jun. 14, 2022

(54) SURGICAL INSTRUMENT DELIVERY SYSTEMS AND RELATED METHODS

(71) Applicant: DePuy Synthes Products, Inc., Raynham, MA (US)

(72) Inventors: Woodward Brown, Monument, CO (US); Rene Haag, Berwyn, PA (US); Mary Schafer, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 148 days.

(21) Appl. No.: 15/622,814

(22) Filed: Jun. 14, 2017

(65) Prior Publication Data

US 2017/0360525 A1 Dec. 21, 2017

Related U.S. Application Data

(60) Provisional application No. 62/350,765, filed on Jun. 16, 2016.

(51) Int. Cl.
*A61B 90/00* (2016.01)
*A61B 50/30* (2016.01)
(Continued)

(52) U.S. Cl.
CPC .............. *A61B 90/08* (2016.02); *A61B 50/30* (2016.02); *A61B 50/33* (2016.02); *A61L 2/26* (2013.01);
(Continued)

(58) Field of Classification Search
CPC ................................ A61L 12/60; B65D 83/10
(Continued)

(56) References Cited

U.S. PATENT DOCUMENTS 4,342,390 A * 8/1982 Mitchell .................... A61L 2/26
206/363
4,926,885 A 5/1990 Hinkle
(Continued)

FOREIGN PATENT DOCUMENTS

CN 1310121 A 8/2001
CN 1849101 A 10/2006
(Continued)

OTHER PUBLICATIONS

Medline.com webpage, https://www.medline.com/product/Lightweight-Surgical-Instrument-Sterilization-Wraps/Sterilization-Wraps/Z05-PF09207?question=&index=P4&indexCount=4, accessed Sep. 12, 2017.
(Continued)

*Primary Examiner* — Anthony D Stashick
*Assistant Examiner* — Raven Collins
(74) *Attorney, Agent, or Firm* — BakerHostetler (57) ABSTRACT

In one aspect of the present disclosure, a sterilization mat is provided that is configured to receive non-sterile surgical instruments, rolled to a rolled configuration, and sterilized while in the rolled configuration. In accordance with another aspect of the present disclosure, a specialized surgical supply kit includes a package that retains surgical supplies having at least one surgical supply identified as a preferred surgical supply by the hospital or surgeon that is to perform the surgery. The surgical supplies are further arranged in a spatial arrangement based on the surgeon who is to perform the surgery.

14 Claims, 6 Drawing Sheets

(51) Int. Cl.
*A61L 2/26* (2006.01)
*B65B 7/00* (2006.01)
*A61B 17/88* (2006.01)
*A61B 17/84* (2006.01)
*A61B 50/33* (2016.01)
*A61B 17/16* (2006.01)
*A61B 17/17* (2006.01)

(52) U.S. Cl.
CPC .............. *B65B 7/00* (2013.01); *A61B 17/164* (2013.01); *A61B 17/1659* (2013.01); *A61B 17/1739* (2013.01); *A61B 17/846* (2013.01); *A61B 17/848* (2013.01); *A61B 17/8866* (2013.01); *A61B 2050/3008* (2016.02); *A61B 2050/314* (2016.02); *A61B 2050/318* (2016.02); *A61B 2090/061* (2016.02); *A61B 2090/0813* (2016.02); *A61L 2202/24* (2013.01)

(58) Field of Classification Search
USPC ............................................ 422/28; 206/363
See application file for complete search history.

(56) References Cited

U.S. PATENT DOCUMENTS

| | | | | |
|---|---|---|---|---|
| 5,022,521 A | * | 6/1991 | Kane | A61B 50/31 206/370 |
| 5,222,600 A | | 6/1993 | Stoddard | |
| 5,427,239 A | | 6/1995 | Hunt | |
| 5,549,868 A | * | 8/1996 | Carlson, II | A61L 2/26 422/1 |
| 5,931,303 A | | 8/1999 | Salvadori | |
| 5,958,337 A | | 9/1999 | Bourne et al. | |
| 6,116,426 A | | 9/2000 | Slonim | |
| 6,158,437 A | | 12/2000 | Vagley | |
| 6,391,260 B1 | * | 5/2002 | Davis | A61L 2/14 206/370 |
| D476,811 S | | 7/2003 | Brookhouse | |
| 9,375,303 B1 | | 6/2016 | Cook et al. | |
| 2009/0236259 A1 | * | 9/2009 | Hicks | A61B 50/30 206/571 |
| 2012/0234781 A1 | | 9/2012 | Cogliano et al. | |
| 2012/0249060 A1 | * | 10/2012 | Stoddard | A61L 2/07 320/107 |
| 2013/0043155 A1 | | 2/2013 | Hartley | |
| 2014/0249515 A1 | | 9/2014 | Martin | |

FOREIGN PATENT DOCUMENTS

| | | |
|---|---|---|
| CN | 101031250 A | 9/2007 |
| CN | 201064493 Y | 5/2008 |
| CN | 201135501 Y | 10/2008 |
| CN | 102630155 A | 8/2012 |
| CN | 103889465 A | 6/2014 |
| CN | 105267032 A | 1/2016 |
| CN | 105287199 A | 2/2016 |
| DE | 29620148 U1 | 1/1997 |
| GB | 1583760 A | 2/1981 |
| GB | 2396550 A | 6/2004 |
| JP | 55-095712 A | 7/1980 |
| JP | 56-116463 A | 9/1981 |
| WO | 2007/037793 A1 | 4/2007 |
| WO | 2015/057999 A1 | 4/2015 |

OTHER PUBLICATIONS

DePuy Synthes, Reamer/Irrigator/Aspirator (RIA) for intramedullary reaming and bone harvesting, Technique Guide, 2015.

Depuy Synthes, Flexible Reamers for Intramedullary Nails, Technique Guide, 2003.

DePuy Synthes, Titanium Cannulated Tibial Nails, Expert Nailing System with Radiolucent Instrumentation, surgical technique guide, 2015, 79 pages.

* cited by examiner

SURGICAL INSTRUMENT DELIVERY SYSTEMS AND RELATED METHODS

CROSS REFERENCE TO RELATED APPLICATIONS

This claims priority to U.S. Provisional Patent Application Ser. No. 62/350,765 filed Jun. 16, 2016, the disclosure of which is hereby incorporated by reference as if set forth in its entirety herein.

BACKGROUND

Orthopedic surgical implantation procedures require surgical supplies that often include not only the implant and bone fasteners in the case of bone fixation, but also the related instrumentation and numerous other surgical instruments. Most of the surgical supplies are required to have a certain size that will fit the anatomy of the patient. Further, some of the surgical supplies are available with different options or configuration, and surgeons and hospitals often have different preference as to which configurations they prefer. Further, the surgical supplies may include specialized instruments that may or may not be used based upon the surgeon preferences and nature of the surgical procedure. Surgical containers are conventionally provided to surgical providers so as to account for these various permutations. For instance, large surgical containers typically include surgical supplies of many different sizes, so that the appropriately sized equipment can be selected and used during the surgical procedure. Further, some of the surgical supplies are provided in the container in different configurations, so that the surgeon can choose certain surgical supplies as a matter of preference over other supplies. Further still, the container may include specialized surgical instruments that may or may not be used during the surgical procedure. Once the surgical supplies for a given surgical procedure have been removed, the surgical container with the unused supplies can be returned to the supplier or stored and reused in another procedure.

In order to ensure that the container includes all possible supplies that may be needed by the surgeon, the container includes, by design, many surgical supplies that will not be used. Accordingly, such surgical containers are bulky and heavy resulting in difficulties from an inventory management and storage standpoint at the surgical provider, and from a shipment standpoint.

Typically, the surgical equipment container is often non-sterile when it arrives at the surgical provider, which can include the hospital, the surgeon, or both. Accordingly, once the surgeon has identified the surgical supplies to be used in a given procedure, the supplies are then sterilized onsite. In particular, the surgical supplies are typically placed in a tray and covered with sterilization wrap. The sterilization wrap can be provided as a woven fabric that can be washed and reused, or as a nonwoven fabric that is typically disposable. The tray and sterilization wrap package is typically placed in an autoclave and subjected to a sterilization agent, such as steam or ethylene oxide, so as to sterilize the surgical supplies in the package. Once the surgical supplies have been sterilized, the package is then transported to the operating room or other storage location. The sterilization wrap is useful to allow the sterilization agent to pass through in the autoclave, but prevent bacteria and other contaminants from entering during transport in non-sterile areas. Unfortunately, the sterilization wrap is subject to tears or other punctures during transport or storage, thereby compromising the sterilization of the surgical supplies. One proposed solution is to place the sterile tray and sterilization wrap into an enclosed protective container. However, such containers are heavy and bulky in an operating room where available space is at a premium.

SUMMARY

In accordance with one aspect of the present disclosure, a method is provided for fabricating a sterilization mat. The method includes the step of defining inner and outer surfaces of a sheet of sterilization fabric that are opposite each other along a transverse direction. Each of the inner and outer ends extends between opposed lateral ends of the sheet of sterilization fabric that are spaced from each other along a lateral direction that is perpendicular to the transverse direction. Each of the inner and outer ends further extend between opposed front and rear ends of the sheet of sterilization fabric that are spaced from each other along a longitudinal direction that is perpendicular to each of the lateral direction and the transverse direction. The method can further include the step of supporting a plurality of pouches that are secured to the sheet, such that the pouches are spaced from each other along the lateral direction. The method can further include the step of causing at least one attachment member to extend from the sheet. Advantageously, each of the pouches is sized to receive a respective surgical supply, such that the sterilization mat is configured to be 1) rolled into a rolled configuration along at least two revolutions about an axis that is oriented along the longitudinal direction, such that a first revolution of the sterilization mat overlaps a second revolution of the sterilization mat along a direction toward the axis, and 2) subjected to a sterilization agent so as to sterilize the received surgical supplies while the sterilization mat is in the rolled configuration.

In accordance with another aspect of the present disclosure, a surgical supply kit can include a package that defines a sterile interior, and a plurality of selected sterile surgical supplies identified for use in a surgical procedure and arranged in the sterile interior in a predetermined spatial arrangement. The selected surgical supplies are selected from a plurality of available surgical supplies configured for use in the surgical procedure. The selected surgical supplies are identified and arranged in the package according to at least one of a surgeon preference and a hospital preference.

BRIEF DESCRIPTION OF THE DRAWINGS

One or more embodiments of the present disclosure will now be described below with reference to the accompanying drawings, in which.

DETAILED DESCRIPTION

Referring initially to FIGS. 1A-3, the present disclosure recognizes that a sterilization mat 20 can be fabricated from a bulk sterilization fabric 22. The sterilization mat 20 has pouches 24 that are sized and configured to receive and retain non-sterile surgical supplies 26, and the sterilization mat 20 can subsequently be rolled into a rolled configuration. While the sterilization mat 20 is in the rolled configuration, the sterilization mat 20 can be subjected to a sterilization agent that travels through the sterilization fabric so as to sterilize the surgical supplies 26 retained in the pouches 24. The sterilized rolled sterilization mat 20 can then be transported into the operating room or other storage location. The sterilization fabric 22 allows the sterilization agent to pass through, but prevents the ingress of bacteria and other contaminants during transportation of the sterilization mat 20 in non-sterile areas after the sterilization step has been performed. Because the rolled sterilization mat 20 does not need to be carried by a tray, and does not surround a tray that contains the surgical supplies, the sterilization mat is less subject to potential sources of tearing or puncture, for instance via contact with sharp edges of the tray during transportation after sterilization. Further, because the sterilization mat 20 is sterilized after being rolled into the rolled configuration, the sterilization mat 20 is subject to less handling and manipulation after sterilization with respect to sterilization mats that are rolled after sterilization, thereby correspondingly reducing activity that can subject the sterilization mat 20 to tearing or puncture during transportation. Additionally, rolling of the sterilization mat 20, and subsequently subjecting the rolled sterilization mat 20 in the rolled configuration consumes less space in the autoclave, and consequently multiple rolls of sterilization mats can be sterilized simultaneously in the autoclave. This reduces overall run time of the autoclave, and correspondingly reduces the amount of time necessary to sterilize large quantities of surgical supplies.

Figure 1A:
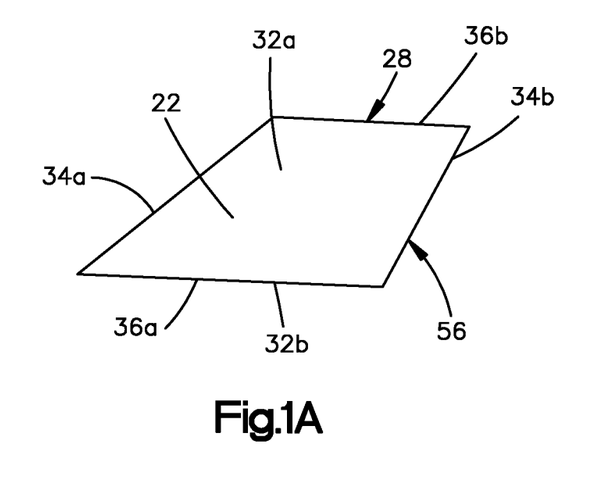
FIG. 1A is a perspective view of a sheet of sterilization wrap in accordance with one aspect of the present disclosure.
Figure 1B:
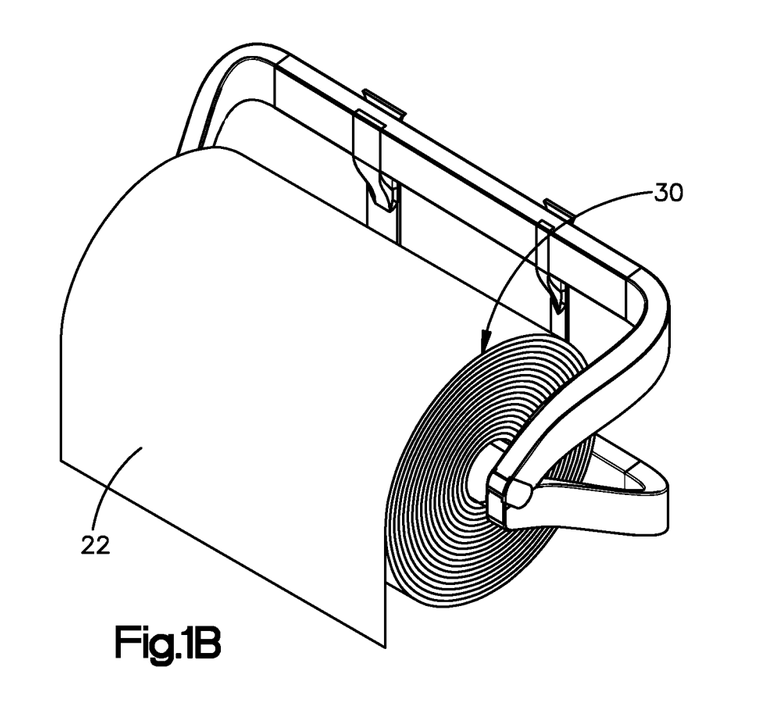
FIG. 1B is a perspective view of a roll of sterilization wrap that can be cut into sheets as illustrated in FIG. 1A.

The sterilization mat 20 can include a sheet 28 of the sterilization fabric 22 that can be cut from bulk sterilization fabric. For instance, the sheet 28 of sterilization fabric 22 can be removed from a roll 30 of bulk sterilization fabric. The roll 30 can have predefined perforations, such that the roll 30 can be torn along the perforation so as to define the sheet 28. Alternatively, the sheet 28 can be cut from the roll 30 using a scissors or any alternative suitable blade. Once the sheet 28 has been removed from the bulk material, the sheet 28 can be shaped as desired. It can be appreciated that the sheet 28 can be a single sheet or a two ply sheet, or can be defined by any number of sheet sections as desired that are either folded over each other or otherwise overlap each other so as to define the sheet 28.

The sheet 28 defines an inner surface 32a and an outer surface 32b that is opposite the inner surface 32a. The inner and outer surfaces 32a-b are opposite each other along a transverse direction T. The sheet 28 further defines opposed lateral ends 34a and 34b that are opposite each other along a lateral direction A that is perpendicular to the transverse direction T. Further, the sheet 28 defines opposed first and second longitudinal ends 36a and 36b, respectively, that are spaced from each other along a longitudinal direction L that is perpendicular to each of the lateral direction A and the transverse direction T. The first longitudinal end 36a can define a front end, and the second longitudinal end 36b can define a rear end. Thus, a forward direction can be defined as a direction from the rear end toward the front end along the longitudinal direction L. Similarly, a rearward direction can be defined as a direction from the front end toward the rear end along the longitudinal direction L.

The sterilization fabric 22 is configured as a spunbonded-meltblown-spunbonded (SMS) nonwoven fabric, which is commercially available inexpensively in bulk. The sterilization fabric 22 is made from a polyolefin that forms three layers laminated to one another. In one example, the sterilization fabric 22 is a polypropylene-based SMS nonwovens, known as blue wrap that has particular applicability when subjected to a sterilization agent in the form of steam. In particular, the SMS polypropylene fabric allows steam to pass through, while preventing ingress of bacteria and other contaminants when in a non-sterile area. It should be appreciated that the sterilization fabric 22 is not intended to be limited to any particular method of manufacture, so long as it allows the sterilization agent (typically a gas) to pass through to the surgical supplies during sterilization, while preventing bacteria and other contaminants to pass through to the surgical supplies when the sterilization fabric is in a non-sterile environment.

Figure 2A:
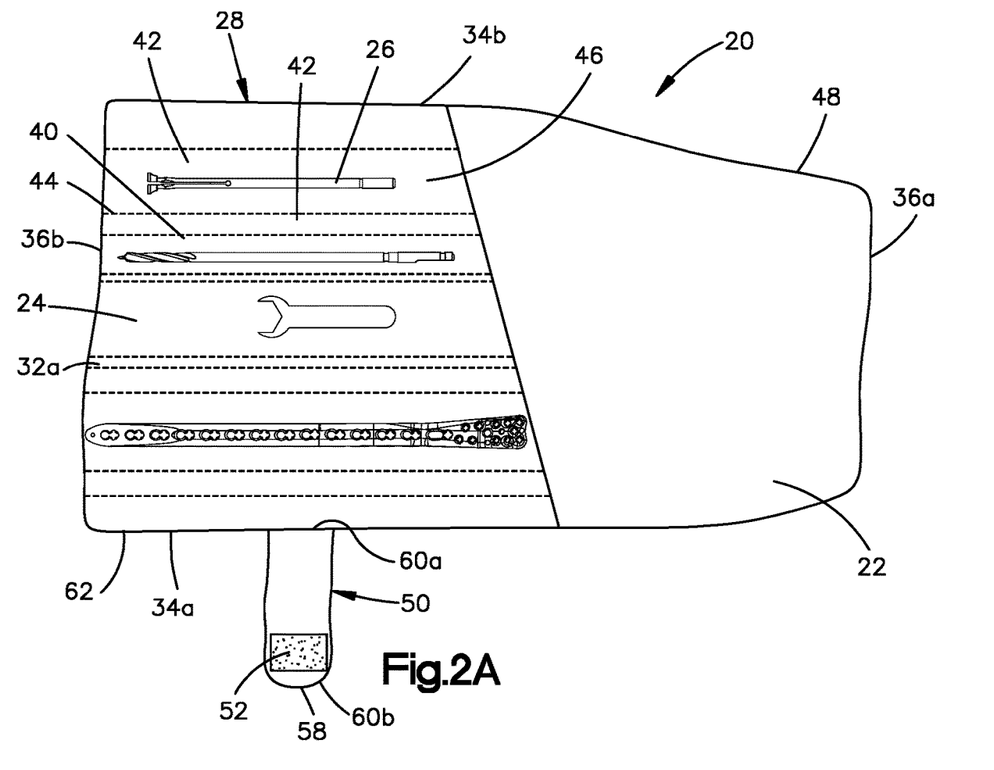
FIG. 2A is a top plan view of a sterilization mat formed from the sheet of sterilization wrap illustrated in FIG. 1A.

The sterilization mat 20 further includes the plurality of pouches 24 supported at the inner surface 32a of the sheet 28. The pouches 24 can be spaced from each other along the lateral direction A. The pouches 24 can have respective lengths along the longitudinal direction L that can be the same or different from each other. In particular, the pouches 24 can be formed from the sterilization fabric 22. For instance, the pouches 24 can be defined by at least one section 40 of the sterilization fabric 22 that is supported by the inner surface 32a. Each of the pouches 24 can be sized to receive a respective surgical supply 26.

In one example, the pouches 24 can be defined by a plurality (e.g., two or more) of sections 40 of fabric 22. In another example, a plurality of the pouches 24 up to all of the pouches 24 can be defined by a single section 40 of the sterilization fabric 22 that is supported by the inner surface 32a. For instance, each of the plurality of sections 40 can define a respective one of the plurality of pouches 24. Alternatively, one or more of the plurality of sections 40 can define more than one of the pouches 24. Thus, it can be said that each of the sections 40 can define at least one of the plurality of the pouches 24. For instance, each of the plurality of sections 40 can be supported at the inner surface 32a at a pair of side support locations 42 that are spaced from each other along the lateral direction A, so as to define the at least one pouch 24 between the side support locations 42, and further between the respective section 40 and the inner surface 32a. In one example, each of the plurality of sections 40 can be attached, such as adhesively attached or stitched, to the inner surface 32a or can be otherwise supported by the inner surface 32a at each of the pair of side support locations 42.

Further, rear ends 44 of the sections 40 can be supported by the inner surface 32a of the sheet 28, for instance, by attaching the rear ends 44 to the inner surface 32a in the manner described above. The rear ends 44 extend between the side support locations 42. In one example, the rear ends 44 can extend to each of the side support locations 42. The sections 40 can define a front end 46 opposite the rear ends 44 in the forward direction. The front ends 46 can remain unattached to the sheet 28, such that the pouches 24 are open at their respective front ends 46. Accordingly, the surgical supplies to be sterilized can be inserted into respective ones of the pouches 24 along the rearward direction.

As described above, adjacent ones of the side support locations 42 along the lateral direction A can define one of the plurality of pouches 24. The pouches 24 can be longer along the longitudinal direction L than they are wide along the lateral direction A. One or more of the sections 40 can be supported by the inner surface 32a at only a pair of side support locations 42, in addition to the rear end 44 as desired. Thus, the sections 40 can define only a single pouch 24. Alternatively, the sections 40 can be supported at a plurality of side support locations 42 that are spaced from each other along the lateral direction A, such that adjacent pairs of the side support locations 42 define respective pouches 24 therebetween. Thus, one or more of the side support locations 42 can define respective sides of adjacent pouches 24.

The front ends 46 of the sections 40, and thus the open ends of the pouches 24, can be spaced from the front end of the sheet 20. Accordingly, the sheet 20 can define a flap 48 that extends from the front end of the sheet 20 to the front ends 46 of the sections 40, and thus to the open ends of the pouches 24. After the surgical supplies have been inserted into the pouches 24, the flap 48 is foldable over the front ends of the pouches 24 prior to rolling the sterilization mat. Thus, the flap 48 can either close the front ends 46 of the pouches 24, or can cover the portion of the surgical instruments in the pouches 24 that extend out of the front ends 46 of the pouches 24. The folded portion of the flap 48 can be attachable to the sheet 20 or the sections 40 once the flap has been folded over. Alternatively, the folded portion of the flap 48 can remain unattached from the sheet and the sections 40, and can be retained in place when the sterilization mat is rolled into the rolled configuration.

Figure 3:
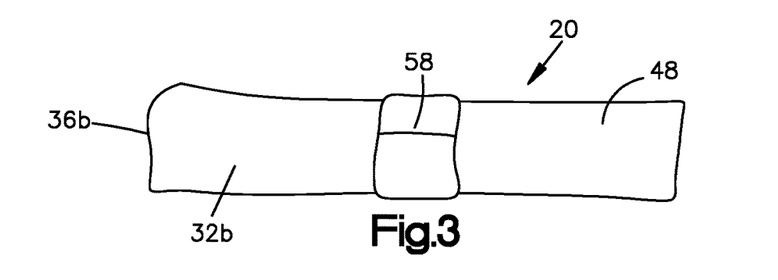
FIG. 3 is a perspective view of the sterilization mat illustrated in FIG. 2, shown in a rolled configuration for insertion into an autoclave.

The sterilization mat 20 can further include an attachment member 50 that is configured to retain the sterilization mat 20 in the rolled configuration. In one example, the attachment member 50 can extend out from a perimeter 56 of the sheet 28 that is defined by the opposed lateral ends 34a and 34b and the opposed longitudinal ends 36a and 36b. The attachment member 50 defines an inner surface 52 that is configured to removably attach to the outer surface 32b of the sheet 20 when the sterilization mat is in the rolled configuration. For instance, the inner surface 52 of the attachment member 50 can define an adhesive or suitable fastener that is configured to attach to any location of the outer surface 32b as desired. Alternatively, the outer surface 32b can define a select complementary attachment member that is configured to attach to the inner surface 52 of the attachment member 50.

In one example, the attachment member 50 can extend out from one of the lateral ends 34a and 34b. For instance, the attachment member 50 can be configured as a tab 58 that extends from the sheet 28 at a first end 60a, and is free from the sheet 28 at a second end 60b. The inner surface of the second end 60b can be configured to attach to the outer surface 32b of the sheet 28 as described above. For instance, the inner surface of the second end 60b can attach via mating of hooks and loops, via an adhesive, or via any suitable attachment mechanism. Alternatively, the tab 58 can have a sufficient length so as to wrap around the rolled sheet 28, and attach to itself. In this regard, the inner surface of the second end 60b can be configured to attach to the outer surface of the first end 60a. The first end 60a of the tab 58 can be attached, such as stitched or adhesively attached, to the sheet 28. Alternatively, the sheet 28 can be cut, bent, folded, or otherwise shaped so as to define the tab 58 that is monolithic with the sheet 28 and extends out from the outer perimeter 56 as desired.

Alternatively, the attachment member 50 can be disposed inside the perimeter 56. For instance, the attachment member 50 can be configured as a select location on the inner surface that is provided with an adhesive or otherwise configured fastener. It should be appreciated, of course, that the sterilization mat 20 can include any number of attachment members 50 as desired that can extend out from the outer perimeter 56 or can be disposed within the perimeter 56 as desired.

The sterilization mat 20 can further include one or more reinforcements 62 at the perimeter 56. The reinforcements 62 can thus be disposed at one or both of the opposed lateral ends 34a and 34b. Alternatively or additionally, the reinforcements 62 can be disposed at one or both of the opposed longitudinal ends 36a and 36b. For instance, the reinforcements 62 can be configured as seams. Thus, the sheet 28 can be folded over itself and stitched so as to define the reinforcements. Alternatively or additionally, one or more stiffeners can be secured to the sheet 28 so as to define the one or more reinforcements 62. In one example, the stiffener can be disposed inside the seamed reinforcement 62. Alternatively, the stiffener can be attached to the sheet in any manner as desired.

During operation, once the surgical supplies 26 have been inserted into the respective pouches 24, the flap 48 is folded rearwardly over the open ends of the pouches 24, thereby covering the exposed portion of the surgical supplies, the open ends of the pouches 24, or both. At least a portion of the surgical supplies 26 and the pouches 24 are thus disposed between the flap 48 and the inner surface 32a of the sheet 28. Next, the sterilization mat 20 can be rolled into a rolled configuration along at least two revolutions. In particular, one of the opposed lateral ends 34a and 34b can be folded such that its outer surface 32b faces the inner surface 32a so as to define a rolled region. The rolled region is then further rolled toward the other of the opposed lateral ends 34a and 34b. Thus, it can be said that the sterilization mat is rolled about a central axis, and in particular along at least two revolutions about the central axis. It is appreciated that the act of rolling the sterilization mat 20 is a dynamic process, and accordingly the central axis translates along the sterilization mat 20 as the sterilization mat is rolled to the rolled configuration. The axis can be oriented along the longitudinal direction L. Once the sterilization mat 20 is in the rolled configuration, a first revolution of the sterilization mat 20 overlaps a second revolution 20 of the sterilization mat along a radial direction that is toward the axis, and can intersect the central axis. The radial direction can be defined by the transverse direction T when the sterilization mat 20 is in the rolled configuration. The attachment member 50 can then be secured to the sheet 28 in the manner described above, as desired.

Next, the sterilization mat 20, including the retained surgical supplies 26 can be inserted in the rolled configuration into an autoclave, whereby a sterilization agent passes through the sterilization fabric 22 and travels into the pouches 24 where it acts on the retained surgical supplies 26 so as to sterilize the retained surgical supplies 26. Once the sterilization process has been completed, the rolled sterilization mat 20 can be transported to an operating room or storage area for use in a surgical procedure. Because the sterilization mat 20 is sterilized after being rolled into the rolled configuration, the sterilization mat 20 is subject to less handling and manipulation after sterilization, thereby reducing activity that can subject the sterilization mat to tearing or puncture during transportation.

Figure 2B:
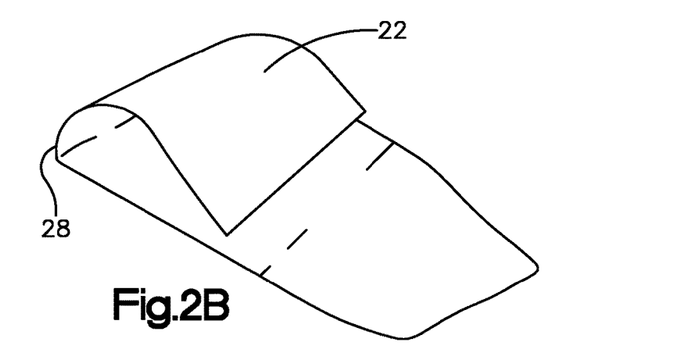
FIG. 2B is a perspective view of the sterilization sheet illustrated in FIG. 1A being formed into the sterilization mat illustrated in FIG. 2A.

It should be appreciated that methods for fabricating the sterilization mat 20 are provided in the present disclosure. For instance, one method can include the step of defining the inner and outer surfaces 32a-b, respectively, of the sheet 28 of sterilization fabric 22 that are opposite each other along the transverse direction T. Each of the inner and outer ends 32a-b extend between opposed lateral ends 34a-b of the sheet 28 of sterilization fabric 22 that are spaced from each other along the lateral direction A, and the opposed front and rear ends of the sheet 28 of sterilization fabric 22 that are spaced from each other along the longitudinal direction L. The method can further include the step of supporting the plurality of pouches 24 at the inner surface 32a, such that the pouches 24 are spaced from each other along the lateral direction A. The method can further include the step of causing the at least one attachment member 50 to extend from the sheet 28. The method can further include the step of providing the sheet 28 from the source of bulk sterilization fabric 22. The method can further include the step of reinforcing one or more up to all of the opposed lateral ends and the opposed longitudinal ends. The reinforcing step can include the step of seaming one or more up to all of the opposed lateral ends and the opposed longitudinal ends.

The step of supporting the plurality of pouches 24 can include the step of supporting the at least one section 40 of the sterilization fabric 22 at the inner surface 32a of the sheet 28 at a pair of side support locations 42 that are spaced from each other along the lateral direction A so as to define the respective pouch 24 between the side support locations 42. The supporting step can further include the step of attaching, for instance adhesively attaching or stitching, the at least one section 40 to the inner surface 32a of the sheet 28 at each of the pair of side support locations 42. The step of supporting the plurality of pouches 24 can further include the step of supporting the rear end 44 of the at least one section 40 to the inner surface 32a of the sheet 28, wherein the rear end 44 extends between the side support locations 42. For instance, the step of supporting the rear end comprises attaching, such as adhesively attaching or stitching, the rear end 44 to the inner surface 32a of the sheet 28.

The step of supporting the plurality of pouches 24 can include the step of supporting the at least one section 40 at a plurality of side support locations 42 spaced from each other along the lateral direction A, such that adjacent pairs of the side support locations 42 define respective pouches 24 therebetween. For instance, the supporting step can include the step of attaching, such as adhesively attaching or stitching, the at least one section 40 to the inner surface 32a at the plurality of side support locations 42. The at least one section 40 can define a single section 40 or a plurality of sections 40. Further, the method can include the step of supporting the at least one section 40 at a plurality of side support locations 42 so as to define a corresponding plurality of pouches 24 therebetween.

The step of causing the at least one attachment member 50 to extend from the sheet 28 can include the step of defining the tab 58 that extends from the sheet 28 at the first end 60a, and is free from the sheet 28 at the second end 60b. For instance, the step of causing the at least one attachment member 50 to extend from the sheet 28 can include the step of attaching the first end 60a of the tab 58 to the sheet 28. Alternatively, the step of causing the at least one attachment member 50 to extend from the sheet 28 can include the step of shaping the sheet 28 such that the tab 58 is monolithic with the sheet 28.

A method of sterilizing surgical supplies can include the steps of inserting the surgical supplies 26 into respective ones of the pouches 24 of the sterilization mat 20. The surgical supplies can include an implant, surgical fasteners, an opening device, fastening instrument, and other related surgical instrumentation. For instance, by way of example only and not limitation, the surgical supplies 26 can include one or more up to all of, in any desired quantity, a drill bit, screwdriver, elevator, retractor, forceps, clamp, saw blade, saw guide, drill guide, hammer, mallet, impactor, sleeve, trocar, aiming arm, cannula, obturator, insertion tool, insertion handle, distractor, rongeur, biter, broach, punch, rasp, pliers, wrench, measuring device, template, burr, shaver, chisel, coupler, chuck, currettes and gouges, reamer, bone lever, scissors, tap, trial, shim, spacer, wire, pin, cutter, pliers, and depth gauge. After the surgical supplies 26 have been inserted into the pouches 24, respectively, the method can include the step of rolling the sterilization mat 20 into the rolled configuration as described above. The method can include the step of subjecting the rolled sterilization mat 20 to a sterilization agent, such that the sterilization agent passes through the sterilization mat 20 and sterilizes the surgical supplies 26. The method can further include the step of, after the inserting step and prior to rolling step, folding the flap 48 over the open front ends of the pouches 24 so as to cover at least one of the front ends and exposed portions of the inserted surgical supplies 26 with the flap 48. The method can further include the step of attaching the second end 60b of the attachment member 50 to the outer surface 32b so as to secure the sterilization mat 20 in the rolled configuration.

Figure 4A:
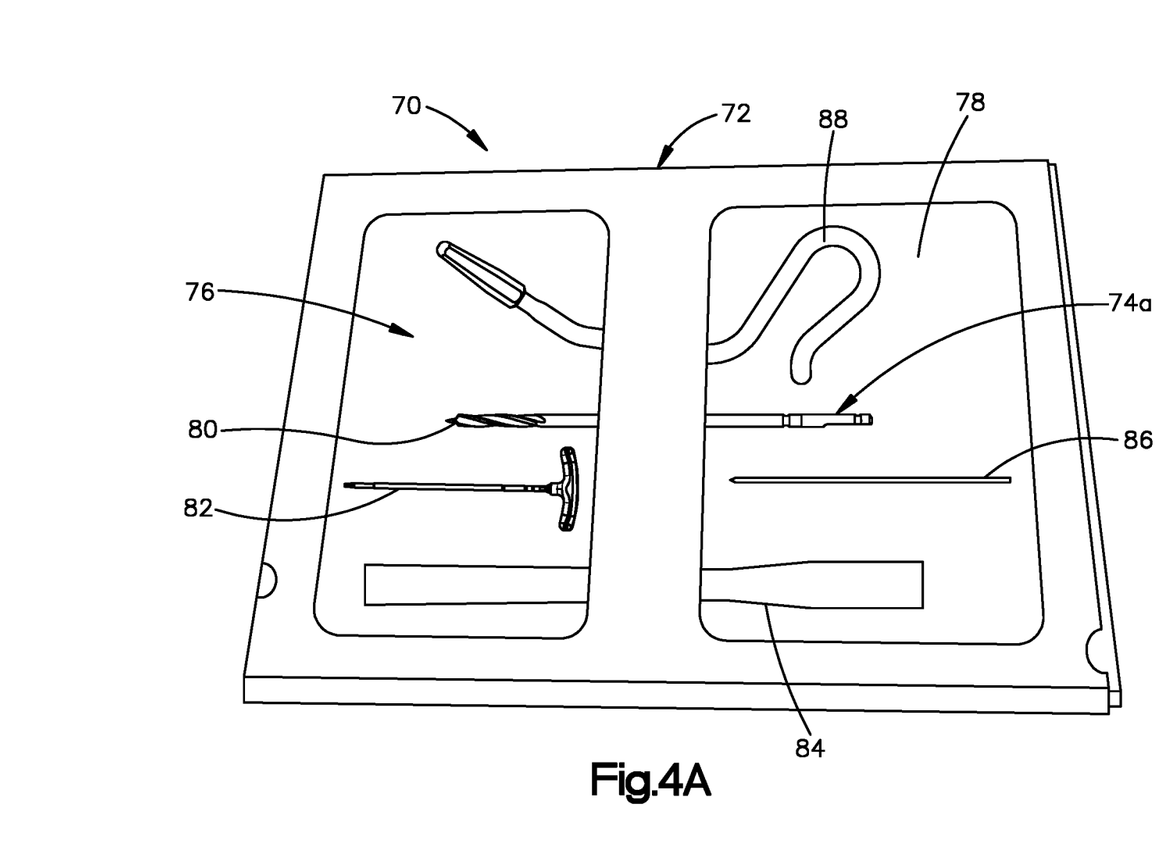
FIG. 4A is a perspective view of an implant kit including a package and a plurality of selected surgical supplies disposed in the package, in accordance with another aspect of the present disclosure.
Figure 4B:
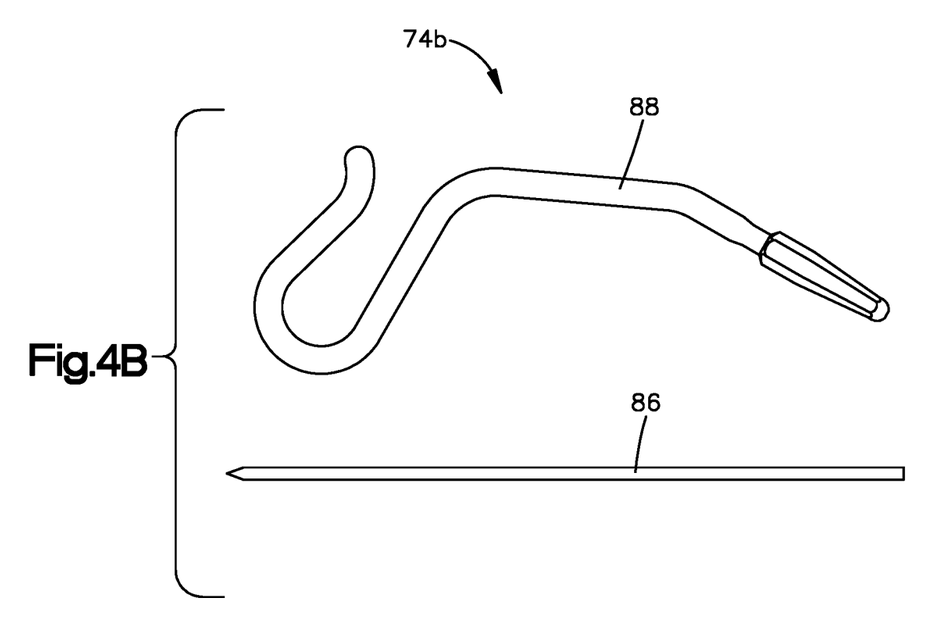
FIG. 4B is a top plan view of an alternative group of surgical supplies with respect to the surgical supplies illustrated in FIG. 4A.
Figure 5A:
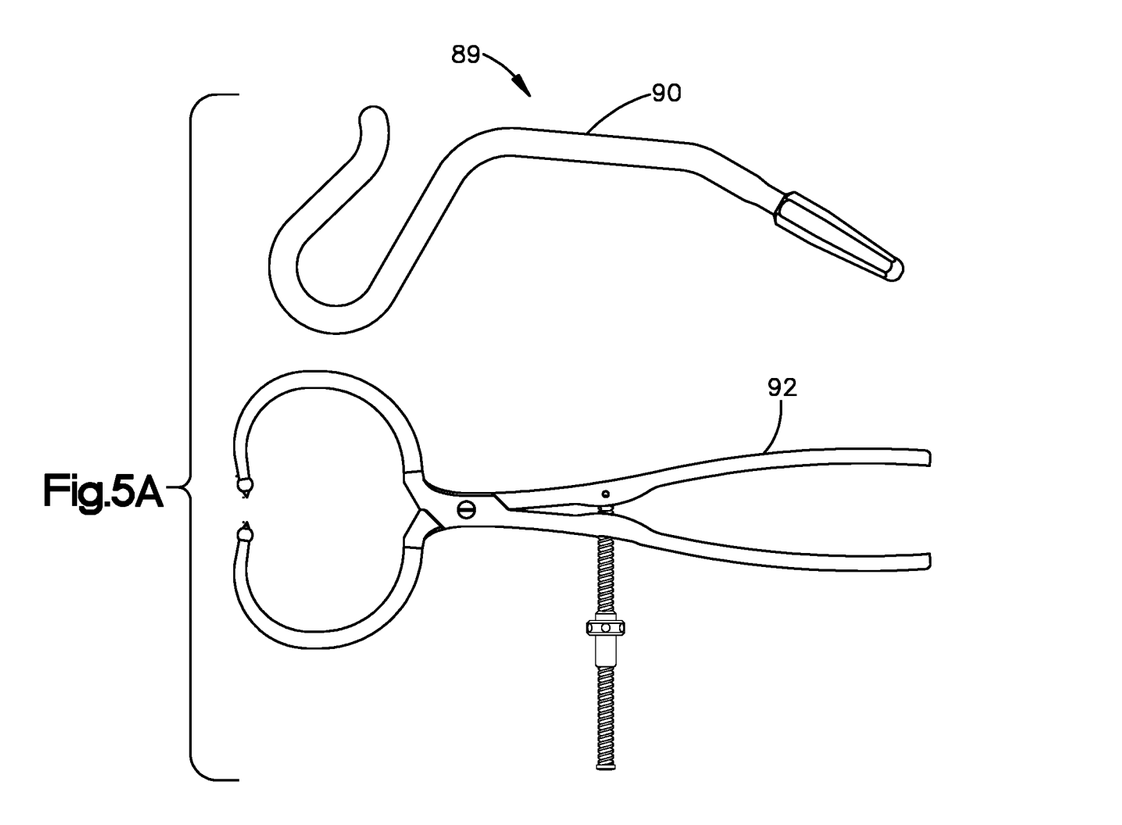
FIG. 5A is a top plan view of optional specialized surgical instruments configured for inclusion in the implant kit illustrated in FIG. 4A.
Figure 5B:
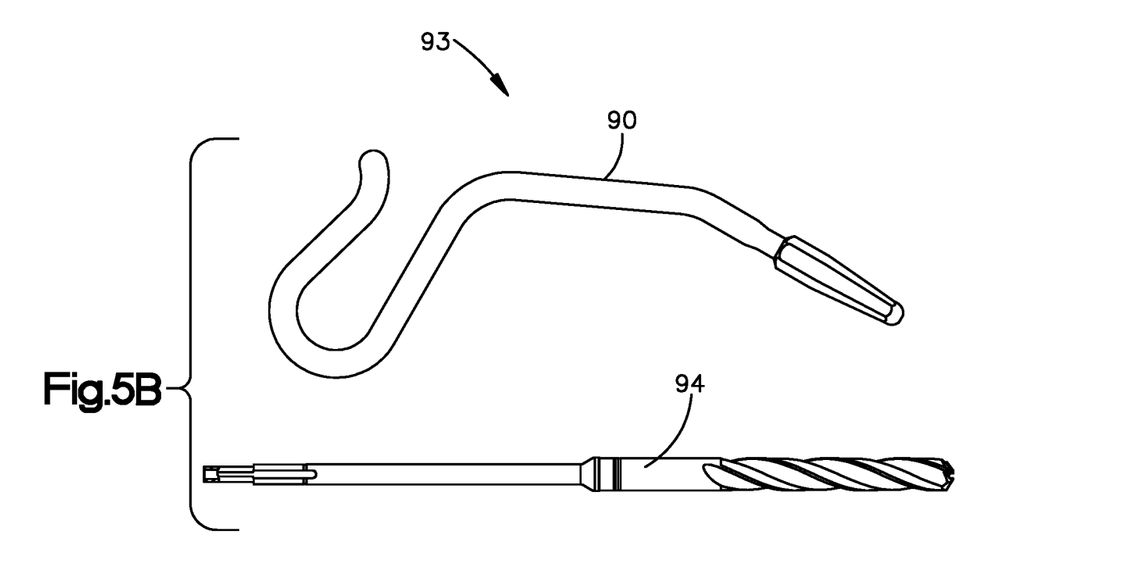
FIG. 5B is a top plan view of optional specialized surgical instruments configured for inclusion in the implant kit illustrated in FIG. 4A.
Figure 5C:
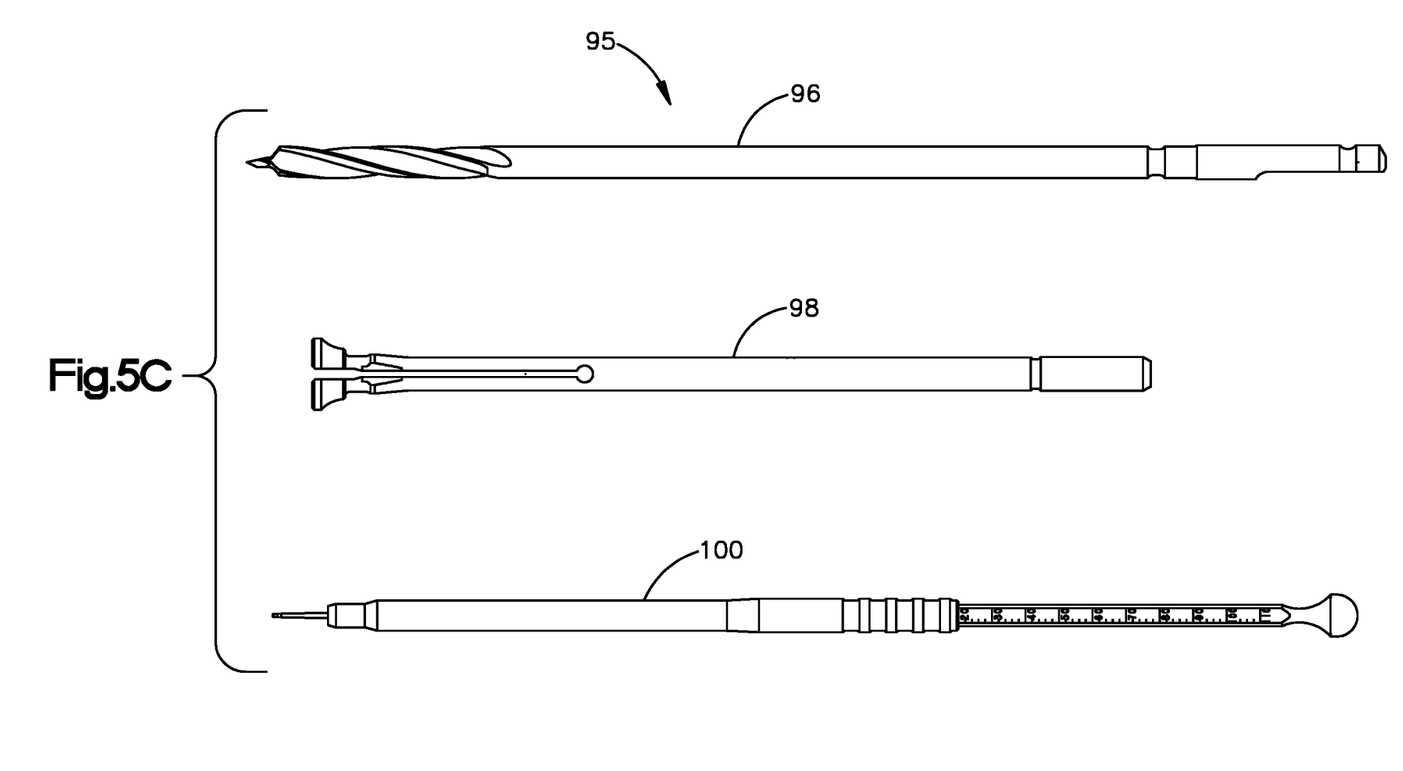
FIG. 5C is a top plan view of optional specialized surgical instruments configured for inclusion in the implant kit illustrated in FIG. 4A.

Referring now to FIGS. 4-5C, the present inventors recognize that several inefficiencies exist in conventional methods and apparatus for delivering surgical supplies to a surgeon who is to perform a specific surgical procedure. Surgical procedures typically include numerous required surgical steps that each require various surgical supplies for the performance of the surgical step. For some of the required surgical steps, surgical technique guides for the surgical procedures identify alternative groups of at least one surgical supply that can be used to perform the required surgical step. The groups among the alternative groups of surgical supplies can be referred to as functional equivalents because they are able to be used to perform the same step of the surgical procedure. The surgeon, based on his or her preference, can determine which of the alternative groups of at least one surgical supply to use when performing the corresponding required surgical step. Still other surgical steps of the surgical procedures are optional. The surgeon, based on his or her preference, can determine whether or not to perform the optional surgical steps at his or her preference. Further still, within the optional surgical steps, the surgical technique guides identify alternative groups of at least one surgical supply that can be used to perform the optional surgical step. The surgeon, based on his or her preference, can determine which of the alternative groups of at least one surgical supply to use when performing the corresponding optional surgical step.

Hospitals currently ensure that the surgical supplies in their surgical supply kits for a surgical procedure include all alternative groups of at least one surgical supply for all require and optional steps of the surgical procedure. Accordingly, the surgical supply kit is likely to include all surgical supplies that a collective group of surgeons might want to use during the surgical procedure no matter the preferences of the individual surgeon within the group of surgeons to be performing the surgical procedure. For this reason, conventional surgical containers are often provided to hospitals that include more surgical supplies than are necessary for a given surgical procedure. As a result, surgical supply kits are large, bulky, and heavy. Accordingly, during the surgical procedure, the surgical supply kits occupy a sizable amount of valuable real state in the operating room. Additionally, the sterilization process of such a large surgical supply kit is time consuming. Further, when the hospitals store the surgical supply kits in inventory, the surgical supply kits occupy a large amount of real estate in the storage area. Alternatively, when the hospital orders the surgical supply kit in anticipation of the surgical procedure, shipping costs are expensive.

Moreover, the present inventors recognize that some surgeons prefer to use equipment that may not exist in the surgical supply kit provided by the hospital. For instance, while a surgical technique guide associated with the surgical procedure may identify particular bone screws to be used with a surgical implant, the surgeon may instead prefer other screws that may be resident in another surgical supply kit. Accordingly, the removal of the preferred screws from the other surgical supply kit will cause the surgical supplies of the other surgical supply kit to be incomplete.

Accordingly, the present disclosure recognizes that a surgical supply kit 70 can be customized for at least one step of given surgical procedure that takes into account the preferences of the surgical provider. That is, the surgical supply kit can include at least one group of at least one surgical supply identified by a surgical technique guide as usable to perform one of the surgical steps of the surgical technique, and does not include at least one alternative group of at least one surgical supply identified by the surgical technique guide as usable to perform the one of the surgical steps. Accordingly, the surgical supply kit 70 can be smaller, less bulky, and lighter than conventional surgical supply kits for surgical procedures. It is further recognized that some of the surgical steps of the surgical procedure require the use of certain surgical supplies without alternatives, and the surgical supply kit 70 can include at least some up to all of the required surgical supplies. A required surgical supply is intended to encompass those surgical supplies that are not subject to the preference of the surgical provider.

The surgical supply kit 70 can include a package 72 that defines an interior 76, and the surgical supplies 74 can be disposed in the interior 76. In one example, the package 72 can include at least one open end for insertion of the surgical supplies 74 into the interior 76. The package 72 can then be closed to secure the plurality of surgical supplies 74 therein. At least one, such as a plurality, of the surgical supplies 74 can be identified for use in an orthopedic surgical procedure according to the preferences of a hospital, the surgeon, or both, wherein the preferences are different than the preferences of at least one other hospital, surgeon, or both. In one example, the surgical supplies 74 in the surgical supply kit 70 can include a portion up to all surgical supplies to be used during a surgical procedure. Thus, it should be appreciated that more than one surgical supply kit 70 can be provided for a given surgical procedure.

In one example, surgical supplies 74 included in the surgical supply kit 70 can include at least one selected surgical supply that is a functional equivalent of at least one alternative surgical supply that is among a plurality of available surgical supplies for performing a particular step of the surgical technique, but the at least one alternative surgical supply is not included in the plurality of selected surgical supplies. The selected and alternative surgical supplies can be earmarked for a required step of the surgical procedure, or can be earmarked for an optional step of the surgical procedure. The selected at least one surgical supply can be preferred by the surgical provider to perform the surgical step over the alternative at least one surgical supply. It is recognized that surgical providers will prefer different ones of the groups of at least one surgical supply for performing a particular surgical step of the surgical technique. Thus, the surgical supplies included in surgical supply kits 70 provided to different surgical suppliers may differ from each other, even though they are identified in the surgical technique guide to perform the same surgical step.

For instance, a publicly available surgical technique guide is included from DePuy Synthes, a company of Johnson & Johnson. The surgical technique guide is entitled "Titanium Cannulated Tibial Nails, Expert Nailing System with Radiolucent Instrumentation" dated 2015. This surgical technique guide is incorporated by reference herein in its entirety. The surgical technique guide sets forth the steps for performing the surgical technique of implanting a tibial nail so as to repair a fractured tibia. Some of the steps are required steps, while others of the steps are optional steps. While certain steps will be identified as examples, it is appreciated that the surgical technique guide includes a plurality of steps for which alternative groups of at least one surgical supply is identified.

As one example, the surgical technique guide identifies at Page 14 the required step of creating an opening in the tibia that extends to the medullary canal of the tibia. The surgical technique guide identifies alternative first and second groups of surgical supplies that can be used to create the opening. The first group of surgical supplies 74a illustrated in FIG. 4A includes a 1) 12.0 mm cannulated drill bit 80 having a large quick coupling, for instance of 190 mm, 2) a handle 82 for wire guides/protection sleeves, 3) a protection sleeve 84, which can be 12 mm in diameter, for a tibial nail, and 4) a 3.2 mm guide wire 86, which can be 400 mm long. The surgical technique guide describes how the surgical supplies of the first group are to be used to create an opening to the medullary canal. The second group of surgical supplies 74b in this example, as illustrated in FIG. 4B, can include 1) a 12.0 mm cannulated awl 88 and 2) the guide wire 86. The surgical technique guide describes the methods of creating an opening to the medullary canal using each of the first and second groups of surgical supplies. While conventional surgical supply kits include the surgical supplies of both the first and second groups, the surgical supply kit 70 of the present disclosure can include the surgical supplies of one of the first and second groups, and not of the other of the first and second groups. It is recognized that some surgeons will prefer the surgical supplies of the first group, while other surgeons will prefer the surgical supplies of the second group. Thus, some surgical supply kits 70 will include the surgical supplies of the first group and not the second group, while other surgical supply kits 70 will include the surgical supplies of the second group and not the first group.

As another example, the surgical technique guide identifies at Page 15 the optional step of reaming the medullary canal. Some surgeons will prefer not to perform this optional step, in which case the surgical supply kit 70 will not include surgical supplies for performing this optional step. Other surgeons will prefer to perform this optional step, in which case the surgical supply kit 70 will include surgical supplies for performing this optional step. The surgical technique guide identifies a plurality of portions of surgical supplies for performing the optional step. The first portion of surgical supplies is a reaming set. The reaming set includes alternative first and second groups of surgical supplies that can be used to create the opening. The first group for the reaming set identified in the technique guide for the optional step is a flexible reamer set for intramedullary (IM) nails. The flexible reamer set is described in a second Technique Guide published by DePuy Synthes and entitled "Flexible Reamers for Intramedullary Nails. To facilitate the insertion of IM nails." This second technique guide is dated 2003, and is incorporated by reference as if set forth in its entirety herein. The second group for the reaming set identified in the technique guide is a reamer/irrigator/aspirator instrument set described in a third Technique Guide published by DePuy Synthes and entitled "Reamer/Irrigator/Aspirator (RIA) For intramedullary reaming and bone harvesting." This third technique guide is dated 2015, and is incorporated by reference as if set forth in its entirety herein.

The second portion of surgical supplies for the optional reaming step includes groups of instruments for performing the reaming step. A first one of the plurality of groups includes a holding device, for guide wires and reaming rods. A second group includes a reaming rod push rod with ball handle. A third group includes a 2.5 mm reaming rod with ball tip, 950 mm, sterile. A fourth group includes a 2.5 mm reaming rod with ball tip and extension, 950 mm, sterile. Accordingly, if the surgeon prefers to perform the reaming step, the at least one surgical supply kit 70 can include one of the groups of the first portion of surgical supplies for the optional step and not include the other one of the groups of the first portion of surgical supplies for the optional step. Similarly, the at least one surgical supply kit can include one of the groups of the second portion of surgical supplies for the optional step, and not include at least one or more up to all other alternative groups of the second portion of surgical supplies for the optional step. It is also recognized that some up to all of the surgical supplies of the at least one surgical supply kit 70 can be shipped to the surgical provider as sterile or non-sterile.

Referring now to FIG. 5A, another known surgical technique in connection with intramedullary nail insertion and reduction can include a standard nail instrument set for nail insertion and reduction. An optional set of surgical supplies 89 can include a broach 90 and a periarticular reduction forceps 92. Thus, the surgical supply kit can include a first group of surgical supplies can include the standard nail instrument set in addition to the broach 90 and the periarticular reduction forceps 92. If this optional set of surgical supplies is not desired, then the surgical kit can include the standard nail instrument set, and does not include the broach 90, and does not include the periarticular reduction forceps 92.

As another example, referring now to FIG. 5B, another known surgical technique in connection with creating an opening in the tibia can include a standard nail instrument set for creating the opening. An optional set of surgical supplies 93 can include the broach 90 and a fluted drill bit 94. Thus, the surgical supply kit can include a first group of surgical supplies can include the standard nail instrument set for creating the opening in addition to the broach 90 and the fluted drill bit 94. If this optional set of surgical supplies is not desired, then the surgical kit can include the standard nail instrument set, and does not include the broach 90, and does not include the fluted drill bit 94.

As still another example, referring now to FIG. 5C, another known surgical technique in connection with locking the intramedullary nail in the medullary canal can include a standard nail instrument set for locking the nail. An optional set 95 of surgical supplies can include a drill bit 96, a drill sleeve 98, and a locking screw measuring device 100. Thus, the surgical supply kit can include a first group of surgical supplies can include the standard nail instrument set for locking the nail in addition to the drill bit 96, the drill sleeve 98, and the locking screw measuring device 100. If this optional set of surgical supplies is not desired, then the surgical kit can include the standard nail instrument set, and does not include the drill bit 96, does not include the drill sleeve 98, and does not include the locking screw measuring device 100.

Further, the surgical supplies can arranged in the interior 76 in a predetermined spatial arrangement that is according to a particular surgeon preference that is different than the preference of at least one other surgeon or hospital. The package 72 can define at least one transparent wall 78 so as to provide visual access to the selected surgical supplies 74 in the interior. In one example, the surgical supplies can be sterilized and placed in the interior 76 of the package 72, where they can remain sterile until the package 72 is opened in the operating room. The package 72 can be configured to be opened such that the selected surgical supplies 74 remain in their spatial arrangement in which they were inserted into the interior 76 of the package 72. The spatial arrangement can include a proximity of one or more of the surgical supplies relative to one or more others of the surgical supplies.

It should be appreciated that the surgical procedure of implantation of a tibial nail is only one example of a wide range of surgical procedures for which the present at least one surgical supply kit 70 is useful. In particular, the at least one surgical supply kit 70 can be useful for any surgical procedure wherein the surgical provider may have a preference of a group of at least one surgical supply among at least one alternative group of the at least one surgical supply to perform at least one of the steps of the surgical procedure. The at least one of the steps of the surgical procedure can be a required step or an optional step.

The preferences of a plurality of surgical providers can be stored in a database. The preferences stored in the database can include the identification of surgical supplies to be used in steps of particular surgical procedures as preferred by surgical providers for different surgical procedures, among a plurality of available alternative surgical supplies for the steps of the particular surgical procedures. The database can further include different spatial arrangements of the surgical supplies as preferred by the surgical providers. Accordingly, when a surgical procedure is to be performed, the surgical supplies that are preferred by the surgical provider who will be performing the surgical procedure can be retrieved from the database. Further, the spatial arrangement of the surgical supplies as preferred by the surgical provider who will be performing the surgical procedure can be retrieved from the database. The surgical supplies can then be inserted into the interior 76 of the package 72 of the at least one surgical supply kit 70, and the surgical supply kit 70 can be shipped to the hospital for use by the surgeon.

Thus, it should be appreciated that a method of fabricating a surgical supply kit can include the step of retrieving a preference of a surgical provider who will be performing the surgical procedure, from the database of preferences of a plurality of surgical providers. The method can further include the step of identifying the plurality of selected surgical supplies 74 for use in a surgical procedure among a plurality of alternative surgical supplies for use in the surgical procedure, wherein the identifying step is in accordance with the retrieved preference of the surgical provider. The method can further include the step of placing the surgical supplies 74 in the interior 76 of the package 72 in the predetermined spatial arrangement, wherein the arrangement is in accordance with the retrieved at least one of a surgeon preference and a hospital preference. The method can further include the step of closing the interior 76 of the package 72. The method can further include the step of, after the closing step, shipping the package to the surgical provider, such as the healthcare provider that is to perform the surgical procedure. The healthcare provider can be a surgical center or a hospital. The method can further include the step of sterilizing the selected surgical supplies 74 prior to the step of closing the interior 76 of the package 72. For instance, the selected surgical supplies 74 can be sterilized prior to inserting the surgical supplies 74 into the interior 76 of the package 72.

In one example, the surgical supplies 74 are sent to the healthcare provider in a non-sterilized state. The surgical supplies 74 can thus be provided to the healthcare provider in the sterilization mat 20. In one example, the surgical supply kit 70 can be configured as the sterilization mat 20 described above.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. For example, it should be appreciated that the surgical instruments included in the sterilization mat 20 can be selected and spatially arranged in the sterilization mat in accordance with the preferences of the surgical provider. It should further be appreciated that the various alternative embodiments described above with respect to one illustrated embodiment can apply to all embodiments as described herein, unless otherwise indicated.

The invention claimed is:

1. A method of sterilizing surgical supplies, the method comprising the steps of:
    inserting the surgical supplies into respective ones of pouches of a sterilization mat;
    rolling the sterilization mat into a rolled configuration; and
    after the rolling step, placing the sterilization mat in the rolled configuration into an autoclave and, after the rolling step, subjecting the sterilization mat to a sterilization agent, such that the sterilization agent passes through the sterilization mat without first passing through any other layers, and sterilizes the surgical supplies,
    wherein the sterilization mat is not carried by a tray.

2. The method as recited in claim 1 further, comprising the steps of:
    providing the sterilization mat prior to the inserting step, the sterilization mat including a sheet of sterilization fabric defined by inner and outer surfaces that are opposite each other along a transverse direction, wherein each of the inner and outer surfaces extends between opposed lateral ends of the sheet of sterilization fabric that are spaced from each other along a lateral direction that is perpendicular to the transverse direction, and opposed front and rear ends of the sheet of sterilization fabric that are spaced from each other along a longitudinal direction that is perpendicular to each of the lateral direction and the transverse direction;
    supporting the pouches of the sterilization mat at the inner surface of the sheet, such that the pouches are spaced from each other along the lateral direction; and
    causing at least one attachment member of the sterilization mat to extend from the sheet,
    wherein rolling the sterilization mat into the rolled configuration comprises rolling the sterilization mat along at least two revolutions about an axis that is oriented along the longitudinal direction, such that a first revolution of the sterilization mat overlaps a second revolution of the sterilization mat along a direction toward the axis.

3. The method as recited in claim 2, wherein the supporting step comprises supporting at least one section of the sterilization fabric at the inner surface of the sheet at a pair of side support locations that are spaced from each other so as to define the respective pouch between the side support locations.

4. The method as recited in claim 3, wherein the supporting step further comprises attaching the at least one section to the inner surface of the sheet at each of the pair of side support locations.

5. The method as recited in claim 3, wherein the supporting step further comprises supporting a rear end of the at least one section to the inner surface of the sheet, wherein the rear end extends between the side support locations.

6. The method as recited in claim 5, wherein a front end of the pouches is open, and the front ends of the pouches are opposite the rear ends of the at least one section along the longitudinal direction.

7. The method as recited in claim 6, wherein the sheet defines a flap that extends forward with respect to the front ends of the pouches, and the flap is foldable over the front ends of the pouches prior to rolling the sterilization mat.

8. The method as recited in claim 7, wherein the at least one section comprises a plurality of sections, and the step of supporting at least one of the plurality of sections at the inner surface comprises attaching at least one of the plurality of sections to the inner surface at the side support locations.

9. The method as recited in claim 2, wherein the causing step comprises defining a tab that extends from the sheet at a first end, and is free from the sheet at a second end.

10. The method as recited in claim 1, further comprising the step of folding a flap of the sterilization mat over open front ends of the pouches so as to cover the front ends with the flap, after the inserting step and prior to the rolling step.

11. The method as recited in claim 10, further comprising securing the sterilization mat in the rolled configuration after the rolling step.

12. The method as recited in claim 11, wherein the securing step comprises attaching an attachment member to an outer surface of the sterilization mat so as to secure the sterilization mat in the rolled configuration.

13. The method as recited in claim 1, wherein the surgical supplies comprise a surgical implant.

14. The method as recited in claim 1, wherein the sterilization mat comprises a polypropylene-based spunbonded-meltblown-spunbonded nonwoven fabric.

* * * * *